United States Patent [19]

Knapp

[11] Patent Number: 4,906,189
[45] Date of Patent: Mar. 6, 1990

[54] MANDIBULAR STAPLE BONE PLATE

[76] Inventor: John G. Knapp, 17485 Vacri, Livonia, Mich. 48152

[21] Appl. No.: 208,748

[22] Filed: Jun. 17, 1988

[51] Int. Cl.⁴ .............................................. A61C 8/00
[52] U.S. Cl. .................................................... 433/173
[58] Field of Search ................ 433/173, 174, 175, 176

[56] References Cited

U.S. PATENT DOCUMENTS

| 2,644,231 | 7/1953 | Brennan | 433/173 |
| 4,214,366 | 7/1980 | Laban | 433/189 |
| 4,516,937 | 5/1985 | Bosker | 433/173 |
| 4,648,841 | 3/1987 | Smith | 433/173 |
| 4,722,687 | 2/1988 | Scortecci | 433/173 |

FOREIGN PATENT DOCUMENTS

| 848162 | 8/1970 | Canada | 433/173 |
| 2302715 | 10/1976 | France | 433/173 |

Primary Examiner—John J. Wilson
Attorney, Agent, or Firm—Basile and Hanlon

[57] ABSTRACT

A mandibular staple bone plate including a support plate having mounting posts attached thereto which extend through the lower jawbone onto which standardized mounting means, embedded within a denture, may be mounted. The mounting means carried thereon engage the top of the mounting posts which extend through the jaw and into the mouth. Additionally, a gauge plate, which may be placed over the mounting posts in a fashion similar to the appliance plate, is used to determine the proper length for the mounting posts prior to mounting the appliance plate on the posts.

22 Claims, 3 Drawing Sheets

MANDIBULAR STAPLE BONE PLATE

BACKGROUND OF THE INVENTION

I. Field of the Invention

The invention is concerned generally with a staple bone plate of the type which is used to retain dental appliances, namely dentures, in contact with the lower jaw.

II. Description of the Relevant Art

Generally, mandibular staple bone plates are used by denture wearers having dentures that become loose as a result of the loss of supporting bone and tissue. The mandibular staple bone plate is used to anchor the lower denture to the lower jawbone. Present designs utilize a relatively standard size staple bone plate for attachment to the lower surface of the jawbone. The plate has rods or screws which project upwardly into or through the jawbone for securing the plate. The rods, extending into the mouth, are threaded over their entire length. This configuration necessitates that special provision be made to avoid irritation of the gums which contact the threads. At this point, however, the standardization of the apparatus ends, and customized attaching means are required, for each patient, in order to mount the denture on the implanted plate. Typically, bridging means are constructed which connect the staple bone plate rods, which project through the jawbone and into the mouth, with the denture. Due to the customized crafting of each mounting assembly, a great deal of time and expense must be incurred by the patient and the doctor.

The present invention is directed to a mandibular staple bone plate which addresses the shortcomings inherent in the relevant art.

SUMMARY OF THE INVENTION

In accordance with the present invention, a mandibular staple bone plate assembly, for use in retaining a dental appliance, namely dentures, within the wearer's mouth comprises a flat elongated support plate having an arcuate configuration which corresponds to the curvature of the lower surface of the front of the jawbone. Fixedly mounted to the support plate are parallel, vertically extending cylindrical mounting posts, each having a first end which is fixedly mounted to the support plate and a second end extending outwardly from the plate. There are at least two posts, each of a length sufficient to extend through the jawbone when the support plate is in abutment with the lower surface of the front of the jawbone. The posts pass through parallel bores formed in the jawbone which correspond in number and size to the posts.

Threads are formed on the lower exterior surface of each post to increase post surface area available for contact with bone tissue. The threads do not extend upwardly far enough to enter the mouth or contact gum tissue which may easily be irritated. The remainder of the post has a smooth outer surface which eliminates irritation and facilitates mounting of a dental appliance.

Additionally, formed in the second end of each mounting post is a threaded bore to which a retaining means may be attached. The retaining means may be utilized to mount, fixedly or releasably, a dental appliance, namely dentures.

One such embodiment of the retaining means may comprise an elongated appliance plate which has an arcuate configuration similar to that of the support plate described above. The appliance plate has receiving means carried on a bottom portion thereof which engage corresponding mounting means disposed on the second ends of the mounting posts. Engagement of the mounting post mounting means with the appliance plate receiving means will rigidly hold the appliance plate within the wearer's mouth in a fixed position relative to the jawbone. The appliance plate will thereby provide a rigid mounting base for a dental appliance, namely dentures.

A second embodiment of the retaining means may comprise a threaded adapter which is threaded into the bore formed in the second end of the mounting post. The adapter is utilized to retain one portion of a standard attachment apparatus which is well known in the art. The other portion of the attachment apparatus is mounted in the underside of the denture thereby providing easy mounting and removal of the denture.

To assure that the mounting posts, extending into the wearer's mouth, are of a proper length to engage the receiving means carried on the bottom portion of the denture, thereby correctly positioning the denture within the mouth, a flat elongated gauge plate, having an arcuate configuration substantially similar to the support plate is provided. The gauge plate may be of any predetermined thickness corresponding to the desired mounting configuration of the denture, and has mounting post bores, which correspond to the mounting post locations. The gauge plate is placed over the second ends of the mounting posts protruding from the lower jaw and the posts are subsequently cut at the top surface of the gauge plate, thereby leaving the mounting posts with a correct protruding length for proper engagement with the denture. The gauge plate is then removed leaving the post ends at a desired, uniform height.

In the case of post breakage, a replacement post may be provided which threadingly engages the mounting post threads at a location below the gum level. The replacement post utilizes a fixing screw which allows the retention of the denture on the new post location.

Other objects and features of the invention will become apparent by reference to the following specification and to the drawings.

BRIEF DESCRIPTION OF THE DRAWINGS

FIGS. 8b, 8c and 8d are examples of alternate forms of standard attachments used with the adapter of FIG. 8a;

FIG. 9b is an example of a standard magnet attachement used with the adapter of FIG. 9a.

DESCRIPTION OF THE PREFERRED EMBODIMENTS

In FIGS. 1-10, there are shown several embodiments of a mandibular staple bone plate assembly of the present invention. A lower jawbone 10 is provided with a staple bone plate assembly, designated generally as 12, to which a dental appliance, namely a denture, may be carried. The staple bone plate assembly 12 comprises several standardized subassemblies, which are described below.

Figure 1:
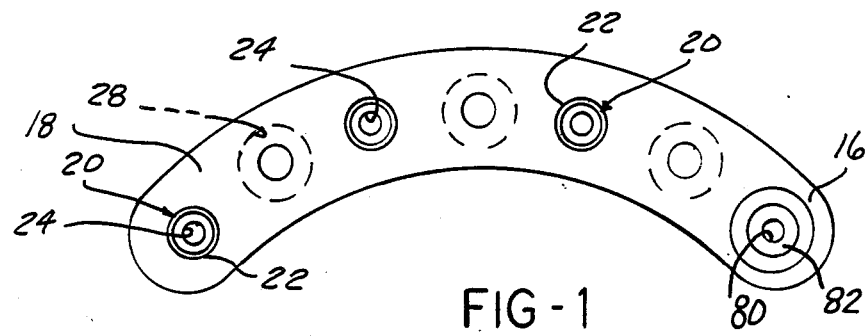
FIG. 1 is a plan view of the support plate of the present invention showing the mounting post and mounting bore locations.
Figure 2:
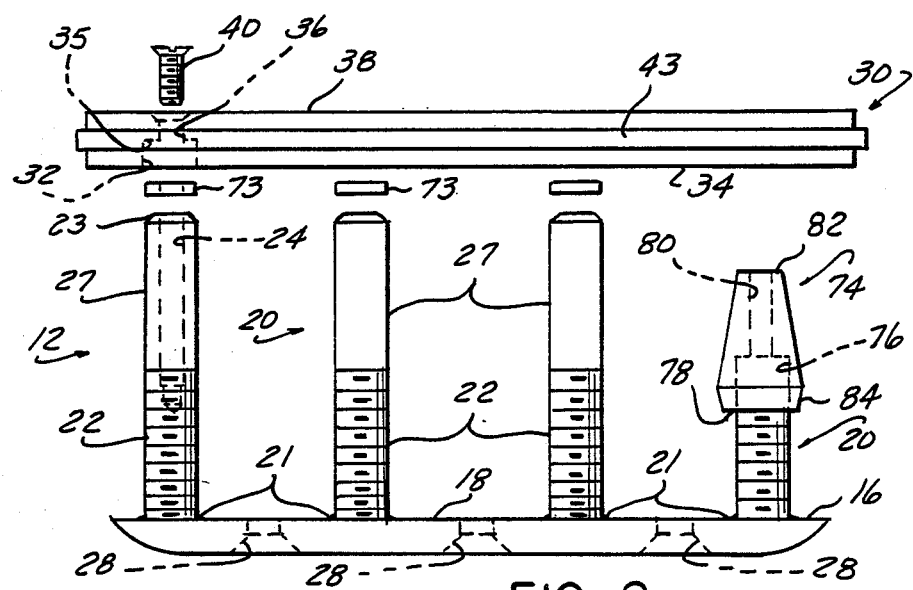
FIG. 2 is an exploded front view of one embodiment of the support plate-mounting post assembly of the present invention.
Figure 3:
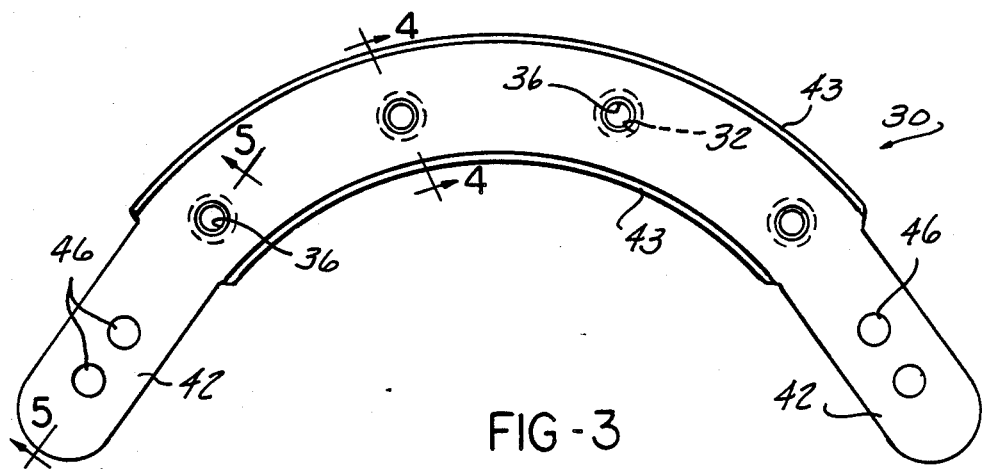
FIG. 3 is a plan view of the appliance plate of the present invention.
Figure 7:
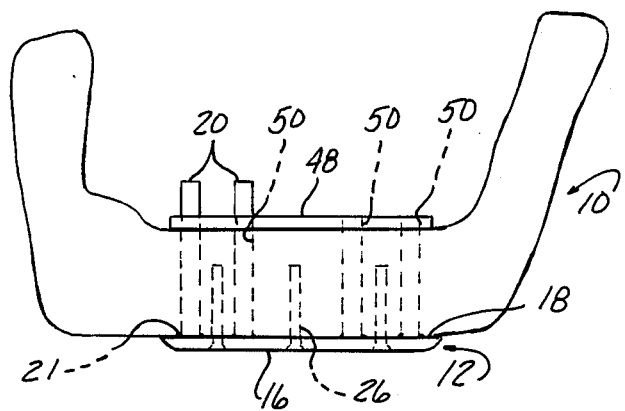
FIG. 7 is a front view of the staple bone plate assembly of the present invention with the gauge plate in position.
Figure 4:
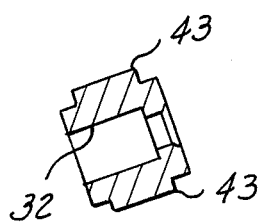
FIG. 4 is a sectional view taken along line 4—4 of FIG. 3.
Figure 5:
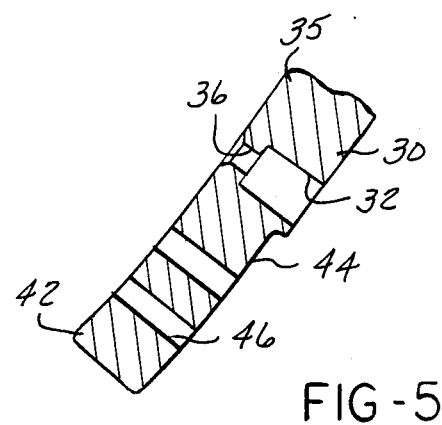
FIG. 5 is a sectional view of the mounting post receiving means of the present invention, taken along line 5—5 of FIG. 3.

FIGS. 1 and 2 show a flat, elongated support plate 16 having an arcuate configuration (FIG. 1) which corresponds to the curvature of the lower frontal surface of jawbone 10. Support plate 16 has a flat top surface 18 which abuts against the bottom of jawbone 10 and carries two or more parallel, outwardly extending, cylindrical mounting posts 20. The mounting posts 20 are permanently affixed to top surface 18, of the support plate 16, by welding or other means suitable for permanently fixing the posts 20 in position. Mounting posts 20 and support plate 16 are preferably made of a titanium alloy material. However, other suitable materials may be used. The mounting posts 20 are preferably positioned at equally spaced locations along the center line of the support plate 16 in a symmetric relationship. The mounting posts 20 extend upwardly, through holes formed in lower jawbone 10, and are of a length sufficient to extend into the patient's mouth when the support plate 16 is in abutment against the lower surface of jawbone 10, as indicated in FIG. 7.

Threads 22 (FIG. 2) may be formed on the exterior surface of mounting posts 20 and extend upwardly from the first ends 21 of mounting posts 20. The threads 22 are utilized to increase the surface area of the mounting posts 20, which are subjected to the growth of replacement tissue. The increased surface area created by the threads 22 allows a stronger bond between the mounting posts 20 and the replacement tissue thereby allowing a greater load to be placed upon the staple bone plate assembly 12 during use.

The threads do not, however, extend upwardly far enough to enter the wearer's mouth or contact gum tissue which is easily irritated. The remainder of the mounting post 20, extending upwardly to second end 23, has a smooth outer surface 27. The smooth surface 27 eliminates any potential for gum irritation caused by a threaded surface entering the mouth and facilitates the mounting of a dental appliance, described in further detail below.

Mounting means are carried by the second ends 23 of mounting posts 20. The mounting means may comprise a threaded bore 24 formed in the second end 23 of each mounting post 20. The threaded bore 24 extends longitudinally through the mounting post 20 from the second end 23 to a position approximately midway of the mounting post 20.

The support plate 16 and mounting posts 20 may be retained in position in lower jawbone 10 solely through the growth of bone tissue around the exterior surface threads 22. Additional strength may be obtained through the use of retaining screws 26, indicated in phantom in FIG. 7, which are inserted upwardly into the lower jawbone 10 through mounting bores 28 formed in support plate 16. Mounting bores 28 may be formed in the support plate 16 at equally spaced positions along the center line of the support plate 16 in a similar fashion to mounting posts 20. The mounting bores 28 are generally equidistant between each mounting post 20 and are bevelled to allow the heads of retaining screws 26 to be seated in a flush position with the bottom of support plate 16.

Retaining means are utilized, in concert with mounting posts 20, to mount, fixedly or releasably, a dental appliance, namely dentures, within a wearer's mouth. A first embodiment of the retaining means utilizes an appliance plate 30 (FIGS. 2-5) which is mountable on the second ends 23 of mounting posts 20 extending above lower jawbone 10 and into the wearer's mouth. Appliance plate 30 is generally elongated, and has an arcuate configuration which is substantially the same shape as that of support plate 16. Receiving means are carried on a bottom portion of appliance plate 30 and engage the mounting means of mounting posts 20. The receiving means may comprise mounting post receiving bores 32 which extend inwardly from the bottom surface 34 of appliance plate 30 to a position approximately midway of the appliance plate thickness. The mounting post receiving bores 32 are formed in positions along the center line of arcuate appliance plate 30, corresponding to the mounting post positions of support plate 16. This allows appliance plate receiving bores 32 to slidingly engage the second ends 23 of mounting posts 20 when installed in the wearer's mouth, as indicated in FIG. 2.

Extending coaxially with mounting post receiving bores 32 are fixing screw bores 36 which extend through the appliance plate 30 from the top surface 38 to coaxially intersect mounting post receiving bores 32. Fixing screw bores 36 are of a diameter corresponding to the diameter of threaded bore 24 formed in the second end 23 of mounting post 20. Fixing screws 40 may be inserted through fixing screw bores 36 to engage mounting post receiving bores 24 when the mounting posts 20 are engaged with the receiving means carried on appliance plate 30.

Support tabs 42 (FIG. 5) extend from the ends of elongated appliance plate 30, in a tangetial orientation to the arc described by appliance plate 30. The tabs have an upwardly angled bottom surface 44 configured to avoid interference with the upwardly inclined portion of the top surface of lower jawbone 10. Additionally, support tabs 42 may be adjusted to accommodate variances in the angle of the jawbone.

Anchoring projections 43 extend outwardly, from the side surfaces of appliance plate 30 and are configured to increase the area of contact between appliance plate 30 and denture 14 when the appliance plate 30 is embedded therein.

In use, the appliance plate 30 is embedded in the base of a denture, with the bottom portion 34 exposed for engagement with the second ends 23 of mounting posts 20, and with the fixing screw bores 36, extending upwardly through the denture. Mounting appliance plate 30 within a wearer's mouth may be accomplished by placing the appliance plate 30, which is embedded in the base of the denture, on the top of mounting posts 20 so that the mounting post ends 23 slidingly engage mounting post receiving bores 32 until the ends 23 abut against shoulder 35. Subsequently, fixing screws 40 are inserted through fixing screw bores 36 to engage the threaded bores 24 of mounting posts 20, thereby retaining appliance plate 30, and its associated denture, into engagement with mounting posts 20.

Figure 8A:
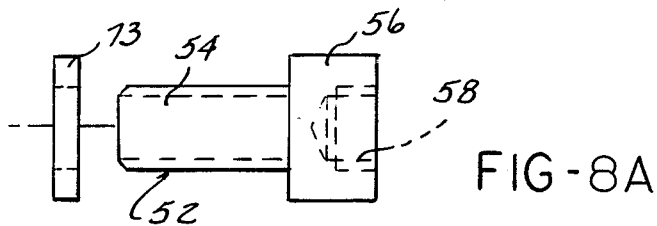
FIG. 8a is an exploded side view of an adapter of the present invention with a spacer attached.
Figure 8B:
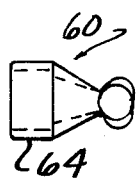
Figure 8C:
Figure 8D:
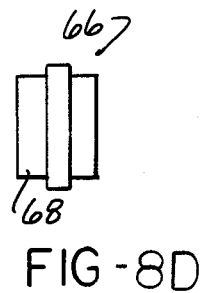

In a second embodiment, the retaining means may utilize adapters 52, shown in FIG. 8a, which are engageable with the second ends 23 of mounting posts 20 to carry a portion of a standard attachment apparatus. The adapters 52 have a first threaded end 54 and a second enlarged end 56 which has a diameter larger than first end 54. A mounting bore 58 extends longitudinally into the adapter 52, from the second end 56, a distance sufficient to engage the male portion of a standard stud-type attachment, indicated in two embodiments, by way of example, at 60 and 62 in FIGS. 8b and 8c, respectively. The mounting bore 58 may be threaded to allow easy engagement with an attachment having a threaded base 64. The female portion of the standard attachment, indicated by way of example at 66 in FIG. 8d, is subsequently embedded in the base portion of a denture with the bottom portion 68 exposed for engagement with the male portions 60, 62 mounted in each adapter 52 of each mounting post 20.

Mounting the denture in the wearer's mouth may subsequently be accomplished by placing the denture, with female attachment portions 66 embedded in position therein, on the top of mounting posts 20; upon which are mounted adapters 52 and male attachment portions 60, 62. The denture is pressed down, into position, to lock the male attachment portions 60, 62 into locking engagement with female attachment portions 66 thereby retaining the denture into engagement with mounting posts 20.

Figure 9A:
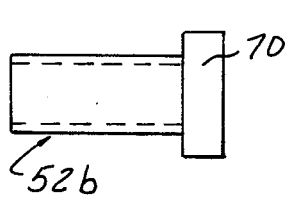
FIG. 9a is a side view of a second embodiment of an adapter of the present invention.
Figure 9B:
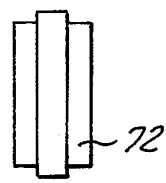
Figure 10A:
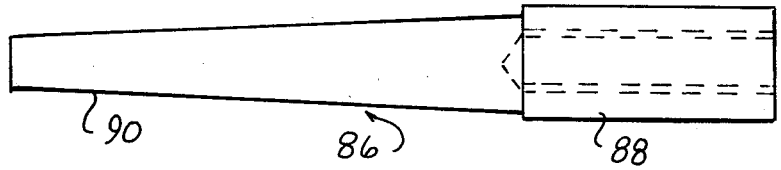
FIGS. 10a and 10b are side and end views, respectively, of the casting post of the present invention.
Figure 10B:
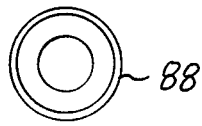

In a third embodiment, the retaining means may utilize adapters 52b, shown in FIG. 9a, which are engageable with the second ends 23 of mounting posts 20 in a similar manner to adapters 52, described above. Adapter 52b, however, is designed with a cap end 70 having properties sufficient to engage a standard retaining magnet, indicated by way of example at 72 in FIG. 9b, well known in the art. The retaining magnet 72 may be embedded in the base portion of a denture, as previously described for the female attachment portion 66 above, and mounting of the denture in the wearer's mouth occurs in the same fashion. Retention of the denture within the mouth occurs through the magnetic attraction between the cap end 70 and magnet portion 72.

Figure 6:
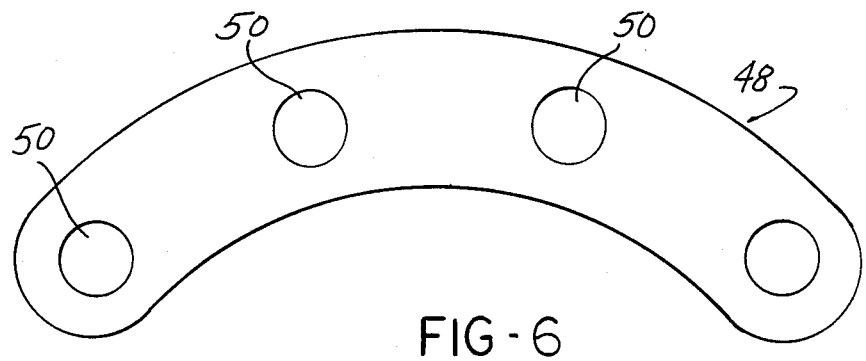
FIG. 6 is a plan view of the gauge plate of the present invention.

To ensure that mounting posts 20 extend the proper distance into the wearer's mouth so that the retaining means and associated denture are properly positioned a gauge plate 48, shown in FIGS. 6 and 7, is used to determine the position at which mounting posts 20 are to be cut following installation. The gauge plate 48 comprises a flat, elongated plate, having an arcuate configuration which is substantially the same as that of support plate 16 and appliance plate 30. Gauge plate 48 has post bores 50, positioned to correspond to the positions of the mounting posts 20 mounted on the support plate 16. The thickness of gauge plate 48 will be chosen to correspond to a predetermined distance at which it is desired to have mounting posts 20 extend above the gum line. This will depend mainly upon the type of retaining means used to mount the denture and the shape and condition of the gums and underlying tissue. The gauge plate is placed over the second ends 23 of the mounting posts 20, the ends of which protrude into the wearer's mouth, and the mounting posts 20 are subsequently trimmed, as shown in FIG. 7, to a length which will provide proper mounting of the denture relative to the jawbone 10.

In cases in which mounting post 20 does not extend far enough into the user's mouth for proper attachment of a particular mounting means, a spacer 73, indicated in FIGS. 2 and 8a, may be used to effectively extend the length of post 20. The spacer 73 is placed between the end 23 of post 20 and the mounting means such as appliance plate 30 (FIG. 2) or adapter 52 (FIG. 8a).

In the event of breakage of mounting post 20, cylindrical replacement peg 74, see FIG. 2, is provided for replacement of post end 23 without the necessity of removing the entire staple bone plate assembly from the jaw. The replacement peg 74 has a mounting post receiving bore 76 extending longitudinally through the peg 74 from a first end 78 to a position approximately midway of the peg 74. Extending coaxially with mounting post receiving bore 76 is a fixing screw bore 80 which extends through peg 74 from its second end 82 to mounting post receiving bore 76.

To install the cylindrical replacement peg 74, mounting post receiving bore 76 is threadingly engaged with the threaded portion 22 of broken mounting post 20. The peg 74 is screwed downwardly onto post 20, to a position in which the lower portion 84 of replacement peg 74 extends below the gum level. In this position, the threaded portion retains the peg 74 in position and presents a smooth outer surface thereby preventing gum irritation. Subsequently, a new mount configured to engage replacement peg 74 (not shown) may be embedded within the denture base, and fixing screw 40 is then inserted through the denture and the new mount, and into engagement with fixing screw bore 80 thereby holding the denture in fixed engagement with mounting post 20 and replacement peg 74.

To facilitate the preparation of the denture, in which the various assemblies disclosed above are embedded, an impression is made of the patient's mouth following implantation of the support plate 16 and mounting posts 20. Casting posts 86, see FIGS. 10a and 10b, may be provided which have a first end 88 configured to resemble the second end 23 of a mounting post 20, and a second anchoring end 90. Prior to casting a positive model of the patient's mouth from the impression taken, the first end 80, resembling the smooth second end 23 of the post 20, may be inserted into the positions in the impressions formed by the actual posts 20 installed in the mouth. Subsequently, a positive casting is made having casting posts 86 formed therein. The posts 86 allow work to be performed on the positive model of the patient's mouth without the breakage problems inherent in casting the entire model, including the posts 20, out of plaster. Once work is completed, the shape of anchoring end 90 allows withdrawal of the post 86 from the model reuse.

While certain embodiments of the invention have been described in detail above in relation to a mandibular staple bone plate, it will be apparent to those skilled in the art that the disclosed embodiment may be modified. Therefore, the foregoing description is to be considered exemplary rather than limiting, and the true scope of the invention is that defined in the following claims.

What is claimed is:

1. A mandibular staple bone plate assembly for use on the lower jawbone, comprising:

a flat, elongated support plate having an arcuate configuration, when viewed in plan, corresponding to the curvature of the lower surface of the jawbone;

at least two, parallel, outwardly extending, cylindrical mounting posts, each having a first end, fixedly mounted to said support plate, and each having a second end extending outwardly from said support plate, said posts being of a length sufficient to extend through the jawbone and into the mouth of the wearer, when said support plate is positioned in abutment with the lower surface of the jawbone wherein said mounting posts comprise a threaded region on the exterior surface thereof, extending from said first end to a position approximately mid way of said post, and an essentially smooth region on the exterior surface thereof extending from said second end to said midway position;

an elongated appliance plate having an arcuate configuration similar to said support plate; and mounting means, disposed between said second ends of said mounting posts and a bottom portion of said appliance plate for attachment of said appliance plate to said second ends of said cylindrical mounting posts;

wherein said appliance plate provides a rigid mounting base for a dental appliance.

2. A mandibular staple bone plate assembly, as defined in claim 1, further comprising:

mounting bores, formed in said support plate;

retaining screws, for attaching said support plate to the lower surface of the jawbone, which extend through said mounting bores and into the lower surface of the jawbone.

3. A mandibular staple bone plate assembly, as defined in claim 1, wherein said mounting means further comprises:

threaded bores extending longitudinally from said second end of said mounting posts to positions approximately midway of said posts;

mounting post receiving bores, configured for sliding engagement with said second ends of said mounting posts, formed in said bottom surface of said appliance plate extending upwardly therethrough, to a position midway of said appliance plate;

fixing screw receiving bores, of a diameter corresponding to said threaded bores in said mounting posts, formed in a top surface of said appliance plate extending downwardly therethrough, in a coaxial relationship with said mounting post receiving bores and into contact with said receiving bores;

fixing screws, engageable with said fixing screw receiving bores and said mounting post threaded bores to retain said appliance plate in fixed engagement with said mounting posts.

4. A mandibular staple bone plate assembly, as defined in claim 1, wherein said mounting means further comprises:

mounting post receiving bores, configured for sliding engagement with said second ends of said mounting posts, formed in said bottom surface of said appliance plate and extending upwardly therethrough to a position midway of said appliance plate;

detent means, mounted to said appliance plate, for engagement with said second ends of said mounting posts to retain said appliance plate in fixed engagement therewith.

5. A mandibular staple bone plate assembly, as defined in claim 1, wherein said appliance plate further comprises:

anchoring projections extending outwardly from side surfaces of said appliance plate for increasing the area of said appliance plate which may be embedded in a dental appliance.

6. A mandibular staple bone plate assembly for use on the lower jaw bone comprising:

a flat, elongated support plate having an arcuate configuration, when viewed in plan, corresponding to the curvature of the lower surface of the jawbone;

at least two, parallel, outwardly extending, cylindrical mounting posts, each having a first end, fixedly mounted to said support plate, and each having a second end extending outwardly from said support plate of a length sufficient to extend through the jawbone and into the mouth of the wearer, when said support plate is positioned in abutment with the lower surface of the jawbone wherein said mounting posts comprise a threaded region on the exterior surface thereof, extending from said first end to a position approximately midway of said post, and an essentially smooth region on the exterior surface thereof extending from said second end to said midway position;

an elongated appliance plate having an arcuate configuration similar to said support plate;

mounting means, disposed between said second ends of said mounting posts and a bottom portion of said appliance plate for attachment of said appliance plate to said second ends of said cylindrical mounting posts; and tabs extending from the ends of said appliance plate, in a tangential orientation to the arc described by said plate, having an upwardly angled bottom surface adjustable to accommodate variances in the angle of the upper surface of the jawbone;

wherein said tabs extend the area of said appliance plate which may be embedded in a dental appliance and said appliance plate provides a rigid mounting base for a dental appliance.

7. A mandibular staple bone assembly for use on the lower jawbone, comprising:

a flat, elongated support plate having an arcuate configuration, when viewed in plan, corresponding to the curvature of the lower surface of the jawbone;

at least two, parallel, outwardly extending, cylindrical mounting posts, each having a first end, fixedly mounted to said support plate, and each having a second end extending outwardly from said support plate of a length sufficient to extend through the jawbone and into the mouth of the wearer, when said support plate is positioned in abutment with the lower surface of the jawbone wherein said mounting posts comprise a threaded region on the exterior surface thereof, extending from said first end to a position approximately mid way of said post, and an essentially smooth region on the exterior surface thereof extending from said second end to said midway position;

an elongated appliance plate having an arcuate configuration similar to said support plate; and mounting means, disposed between said second ends of said mounting posts and a bottom portion of said appliance plate for attachment of said appliance plate to said second ends of said cylindrical mounting posts, said mounting means comprising:

(a) threaded bores extending longitudinally from said second end of said mounting posts to positions approximately midway of said posts;

(b) mounting post receiving bores, configured for sliding engagement with said second ends of said mounting posts, formed in said bottom surface of said appliance plate extending plate;

(c) fixing screw receiving bores, of a diameter corresponding to said threaded bores in said mounting posts, formed in a top surface of said appliance plate extending downwardly therethrough, in a coaxial relationship with said mounting post receiving bores and into contact with said receiving bores; and (d) fixing screws, engageable with said fixing screw receiving bores and said mounting post threaded bores to retain said appliance plate in fixed engagement with said mounting posts;

a flat, elongated gauge plate, having an arcuate configuration substantially similar to said appliance plate, of a thickness corresponding to the depth of associated receiving means, and mounting post bores corresponding to the post locations of said staple plate and said receiving means of said appliance plate;

said gauge placeable over said second ends of said mounting posts extending upwardly through said jawbone and into abutment with the top surface of said jaw, said second ends of said mounting posts extending through, and above, said gauge plate may be cut; and wherein said gauge plate is removed thereby leaving mounting post ends of a length required to support said appliance plate in a desired relationship above said jawbone.

8. A mandibular staple bone plate assembly for use on the lower jawbone, comprising:

a flat, elongated support plate having an arcuate configuration, when viewed in plan, corresponding to the curvature of the lower surface of the jawbone;

mounting bores, formed in said support plate;

retaining screws for attaching said support plate to the lower surface of the jawbone, extending through said mounting bores;

at least two, parallel outwardly extending cylindrical mounting posts, each having a first end fixedly mounted to said support plate, each having a second end extending upwardly and of a length sufficient to extend through the jawbone and into the mouth of a wearer when said support plate is in abutment with the lower surface of the jawbone;

a threaded surface formed on the exterior surface of said mounting posts, extending from said first end to a position approximately midway of said post;

a smooth surface formed on the exterior surface of said mounting posts, extending from said second end to a position below the surface of the gum tissue in a wearer's mouth;

an elongated appliance plate having an arcuate configuration similar to said support plate;

tabs extending from the end of said appliance plate in a tangential orientation to the arc described by said plate, having an upwardly angled bottom surface, adjustable to accommodate variances in upper jawbone angles;

anchoring projections extending outwardly from side surfaces of said appliance plate for increasing the area of said appliance plate which may be imbedded in a dental appliance;

threaded bores extending longitudinally from said second ends of said mounting posts to positions approximately midway of said posts;

mounting post receiving bores configured for sliding engagement with said second ends of said mounting posts, formed in said bottom surface of said appliance plate, extending upwardly therethrough to a position midway of said appliance plate;

fixing screw receiving bores, of a diameter corresponding to said threaded bores in said mounting posts formed in a top surface of said appliance plate, extending downwardly therethrough in a coaxial relationship with said mounting post receiving bores and into contact therewith;

fixing screws, engageable with said fixing screw receiving bores and said mounting posts threaded bores to retain said appliance plate in fixed engagement with said mounting posts;

a flat elongated gauge plate, having an arcuate configuration substantially similar to said appliance plate, a thickness corresponding to the depth of said receiving bores in said appliance plate, and mounting post bores corresponding to the post location of said staple plate and said post receiving bores of said appliance plate;

wherein said gauge plate may be placed over said second ends of said mounting posts which extend upwardly through said jawbone;

wherein said second ends of said mounting posts extending through, and above, said gauge plate may be cut; and wherein said gauge plate may be removed thereby providing mounting post ends of a length required to engage said appliance plate into the desired relationship above said jawbone.

9. A mandibular staple bone plate assembly for use on the lower jawbone, comprising:

a flat, elongated support plate having an arcuate configuration, when viewed in plan, corresponding to the curvature of the lower surface of the jawbone;

at least two, parallel, outwardly extending, cylindrical mounting posts, each having a first end, fixedly mounted to said support plate, and each having a second end extending outwardly from said support plate of a length sufficient to extend through the jawbone and into the mouth of the wearer, when said support plate is positioned in abutment with the lower surface of the jawbone wherein said mounting posts comprise a threaded region on the exterior surface thereof, extending from said first end to a position approximately mid way of said post, and an essentially smooth region on the exterior surface thereof extending from said second end to said midway position;

an elongated appliance plate having an arcuate configuration similar to said support plate; and mounting means, disposed between said second ends of said mounting posts and a bottom portion of said appliance plate for attachment of said appliance plate to said second ends of said cylindrical mounting posts, wherein said appliance plate provides a rigid mounting base for a dental appliance;

a flat elongated gauge plate, having an arcuate configuration substantially similar to said appliance plate, a thickness corresponding to the depth of receiving bores in said appliance plate, and mounting post bores corresponding to the post location of said staple plate and said post receiving bores of said appliance plate;

wherein said gauge plate may be placed over said second ends of said mounting posts which extend upwardly through jawbone;

wherein said second ends of said mounting posts extending through, and above, said gauge plate may be cut; and wherein said gauge plate may be removed thereby providing mounting post ends of a length required to engage said appliance plate into the desired relationship above said jawbone.

10. A mandibular staple bone plate assembly, as defined in claim 9, further comprising:

a flat elongated gauge plate, having an arcuate configuration substantially similar to said support plate, a having a predetermined thickness, and mounting post through bores corresponding to the post locations of said staple plate assembly;

wherein said gauge plate may be slidingly over said second ends of said mounting posts which extend upwardly through the jawbone;

wherein said second ends of said mounting posts extending through, and above, said gauge plate may be cut; and wherein said gauge plate may be removed thereby providing mounting post ends of a length required to support said appliance plate into a desired relationship above the jawbone.

11. A mandibular staple bone plate assembly for use on the lower jawbone, comprising:

a flat, elongated support plate having an arcuate configuration, when viewed in plan, corresponding to the curvature of the lower surface of the jawbone;

at least two, parallel, outwardly extending cylindrical mounting posts, each having a first end fixedly, unitarily mounted to said support plate and a second end extending outwardly from said support plate, said posts of a length sufficient to extend through the jawbone and gum and into the mouth of the wearer when said support plate is positioned in abutment with the lower surface of the jawbone;

a threaded region on an exterior surface of each mounting post, said threaded region extending from said first end to a position approximately midway of said posts, to correspond with the bony portion of the jawbone when said assembly is positioned in abutment with the lower surface of the jawbone; and a smooth region on said exterior surface of each mounting post, extending from said second end to a position approximately midway of said mounting posts, to correspond with the gum tissue portion of the jaw, when said assembly is positioned in abutment with the lower surface of the jawbone.

12. A mandibular staple bone plate assembly, as defined in claim 11, further comprising means for retaining a dental appliance in engagement with said assembly.

13. A mandibular staple bone plate assembly, as defined in claim 12, said retaining means further comprising:

threaded mounting bores extending longitudinally from said second end of said mounting posts to positions approximately midway of said posts;

adapters, having a first threaded end portion and a second end portion having a diameter larger than said first end portion, a mounting bore extending longitudinally from said second end portion, said first end portion of said adapter threadably engageable with said threaded mounting bore;

wherein said mounting bore is configured to receive a first portion of a standardly available stud-type attachment;

wherein said dental appliance is configured to receive a second portion of a standardly available stud-type attachment; and wherein said dental appliance is fixable to said second ends of said mounting posts by engaging said second portions of the stud-type attachments, received in the appliance, with the first portions of the stud-type attachments, received in said mounting bores of said adapters.

14. A mandibular staple bone plate assembly, as defined in claim 12, said retaining means further comprising:

threaded mounting bores extending longitudinally from said second end of said mounting posts to positions approximately midway of said posts;

adapters, having a first threaded end portion and a second end portion having properties sufficient to engage a standardly available retaining magnet, said first end portion of said adapter threadably engageable with said threaded mounting bore;

wherein said dental appliance is configured to receive a standardly available retaining magnet; and wherein said dental appliance is fixable to said second ends of said mounting posts by magnetically engaging said retaining magnet, received in the appliance, with said second end portion of said adapter.

15. A mandibular staple bone plate assembly, as defined in claim 11, further comprising:

a replacement peg, having a longitudinally extending body, first and second ends, a mounting post receiving bore extending longitudinally from said first end to a position approximately midway of said peg, a fixing bore extending, coaxially with said mounting post receiving bore, from said second end to a position intersecting said mounting post receiving bore, said mounting post receiving bore engageable with an exterior portion of a broken mounting post to provide a replacement mounting post without the necessity of removing said staple bone plate assembly from the jaw.

16. A mandibular staple bone plate assembly, as defined in claim 15, wherein said replacement peg further comprises a smooth outer surface.

17. A mandibular staple bone plate assembly, as defined in claim 15, wherein said mounting post receiving bore is threaded for engagement with an exterior threaded portion of said broken mounting post.

18. A mandibular staple bone plate assembly, as defined in claim 15, further comprising:

a replacement retaining means insertable into the dental appliance; and a fixing screw insertable through the dental appliance and said retaining means, into engagement with said fixing bore of said replacement peg to retain said retaining means and the dental appliance in engagement with said replacement peg.

19. A mandibular staple bone plate assembly, as defined in claim 11, further comprising:

casting posts corresponding in number to said mounting posts, said casting posts having a longitudinally extending body with a first and a second end, said first end configured to resemble said second end of said mounting posts, and said second end having a gradually tapering configuration for anchoring said second end in to a plaster cast of the mouth.

20. A mandibular staple bone plate assembly for use on a lower jawbone, comprising:

a flat elongated support plate having an arcuate configuration, when viewed in plan, corresponding to the curvature of the lower surface of the jawbone;

at least two, parallel outwardly extending cylindrical mounting posts, each having a first end fixedly mounted to said support plate and a second end extending outwardly from said support plate, said posts of a length sufficient to extend through the jawbone and into the mouth of the wearer when said support plate is positioned in abutment with the lower surface of the jawbone;

a threaded region on the exterior surface of each mounting post, said threaded region extending from said first end to a position approximately midway of said posts, to correspond with the bony portion of the jawbone when said assembly is positioned in abutment with the lower surface of the jawbone;

means for retaining a dental appliance in engagement with said assembly; and removable spacers positioned between, and in contact with, said second ends of said mounting posts and said mounting means, said spacers having a configuration, when viewed in plan, essentially corresponding to the configuration of said second ends of said mounting posts, for increasing the length of said mounting posts to a predetermined length.

21. A method of preparing a cast impression of a mouth having a mandibular staple bone plate assembly inserted therein, comprising the steps of:

forming a negative impression of the mouth, said impression having depressions formed by the mounting posts of said staple bone plate assembly;

inserting a casting post into each of said depressions, said casting post having a longitudinally extending body with a first and a second end, said first end configured to resemble said second end of said mounting post and said second end having a gradually tapering configuration for anchoring said second end into a positive cast of the mouth; and forming a positive casting from said negative impression with said casting posts fixedly inserted therein, said first end portion extending outwardly from said positive casting to substantially resemble the mounting posts of said staple bone plate assembly in the mouth, and said second tapered end portion securely and removably embedded in said casting.

22. A method of producing a standardized mandibular staple bone plate assembly for use on the lower jawbone, comprising the steps of:

forming a flat, elongated support plate having an arcuate configuration, when viewed in plan, corresponding to the curvature of the lower surface of the jawbone;

forming two or more parallel, outwardly cylindrical mounting posts, each having a first end, fixedly mounted to said support plate prior to installation into a patient's jaw, and each having a second end extending outwardly from said support plate, in a parallel relationship to said other mounting post, a length sufficient to extend through the jawbone and into the mouth of the wearer, when said support plate is positioned in abutment with the lower surface of the jawbone;

forming a flat, elongated appliance plate having an arcuate configuration when viewed in plan, substantially similar to said support plate, mounting means, located between said second ends of said mounting posts and said appliance plate, at positions along said arcuate appliance plate determined by the locations of said second ends of said parallel, outwardly extending cylindrical mounting posts, prior to installation of said support plate or said appliance plate in a patient's jaw, for attachment of said appliance plate to said second ends of said cylindrical mounting posts;

wherein said appliance plate provides a rigid mounting base for a dental appliance.

* * * * *